United States Patent
Jani et al.

(10) Patent No.: US 9,738,572 B2
(45) Date of Patent: Aug. 22, 2017

(54) METHODS AND APPARATUSES FOR SELECTIVE HYDROGENATION OF OLEFINS

(71) Applicant: UOP LLC, Des Plaines, IL (US)

(72) Inventors: Priyesh Jayendrakumar Jani, Gurgaon (IN); Soumendra Mohan Banerjee, New Delhi (IN); David W. Ablin, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 332 days.

(21) Appl. No.: 14/513,764

(22) Filed: Oct. 14, 2014

(65) Prior Publication Data
US 2016/0102256 A1    Apr. 14, 2016

(51) Int. Cl.
C07C 5/03    (2006.01)
C10G 45/00   (2006.01)
B01J 19/24   (2006.01)
C07C 5/02    (2006.01)

(52) U.S. Cl.
CPC ............. *C07C 5/03* (2013.01); *B01J 19/245* (2013.01); *C07C 5/02* (2013.01); *C10G 45/00* (2013.01)

(58) Field of Classification Search
CPC .... C07C 5/00; C07C 5/02; C07C 5/03; C10G 45/00
See application file for complete search history.

(56) References Cited

U.S. PATENT DOCUMENTS

| | | | | |
|---|---|---|---|---|
| 3,409,515 A | * | 11/1968 | Baird | B01D 3/00 159/16.1 |
| 3,869,377 A | * | 3/1975 | Eisenlohr | C10G 69/08 208/66 |
| 4,333,817 A | * | 6/1982 | O'Brien | C01B 3/50 208/101 |
| 5,658,453 A | | 8/1997 | Russ | |
| 5,821,397 A | * | 10/1998 | Joly | B01J 37/20 585/258 |
| 6,284,128 B1 | | 9/2001 | Glover | |

(Continued)

FOREIGN PATENT DOCUMENTS

CN    102051231 B    11/2013

OTHER PUBLICATIONS

Wauquier, Jean-Pierre. (2000). Petroleum Refining, vol. 2—Separation Processes. (pp. 284). Editions Technip. Chapter 5, p. 284.*

(Continued)

*Primary Examiner* — Sharon Pregler
*Assistant Examiner* — Alyssa L Cepluch

(57) ABSTRACT

Methods and apparatuses for selective hydrogenation of olefins are provided. The method for selective hydrogenation of olefins comprises reacting a hydrocarbonaceous feedstock comprising olefins and aromatic compounds with hydrogen in a reaction zone. The reaction contains a catalyst producing a reaction zone product stream comprising aromatic compounds. The reaction zone product stream is passed to a flash vessel, recovering a first product stream and a second product stream from the flash vessel. The first product stream is passed to a liquid jet eductor, whereas the second product stream comprising aromatic compounds having a reduced concentration of olefins is subsequently recovered.

19 Claims, 1 Drawing Sheet

(56) References Cited

U.S. PATENT DOCUMENTS

| | | | |
|---|---|---|---|
| 6,548,721 B1* | 4/2003 | Mc Culloch | C07C 7/163 585/276 |
| 6,977,317 B1 | 12/2005 | Frey | |
| 8,753,503 B2 | 6/2014 | Krupa | |
| 2013/0158311 A1 | 6/2013 | Serban | |
| 2014/0109465 A1 | 4/2014 | Coppola | |

OTHER PUBLICATIONS

Cao, "Selective Hydrogenation for Removal of Olefins from Reformate", Petroleum Refinery Engineering, 2010, v. 40, p. 18-21, ISSN: 1002106X.

Nan, "Study on PD-based Catalysts for Selective Hydrogenation of Olefin in Reformate", Acta Petrolei Sinica (Petroleum Processing Section), v.22, n.5, p. 20-25, Oct. 25, 2006; ISSN: 10018719; Publisher: China International Book Trading Corp.

Nan, "Preparation of UDO-01 Catalyst for Selective Hydrogenation of Olefin in Reformate", Petroleum Processing and Petrochemicals, v.38, n.1, p. 28-33, Jan. 2007; ISSN: 10052399; Publisher: Research Institute of Petroleum Processing, SINOPEC.

* cited by examiner

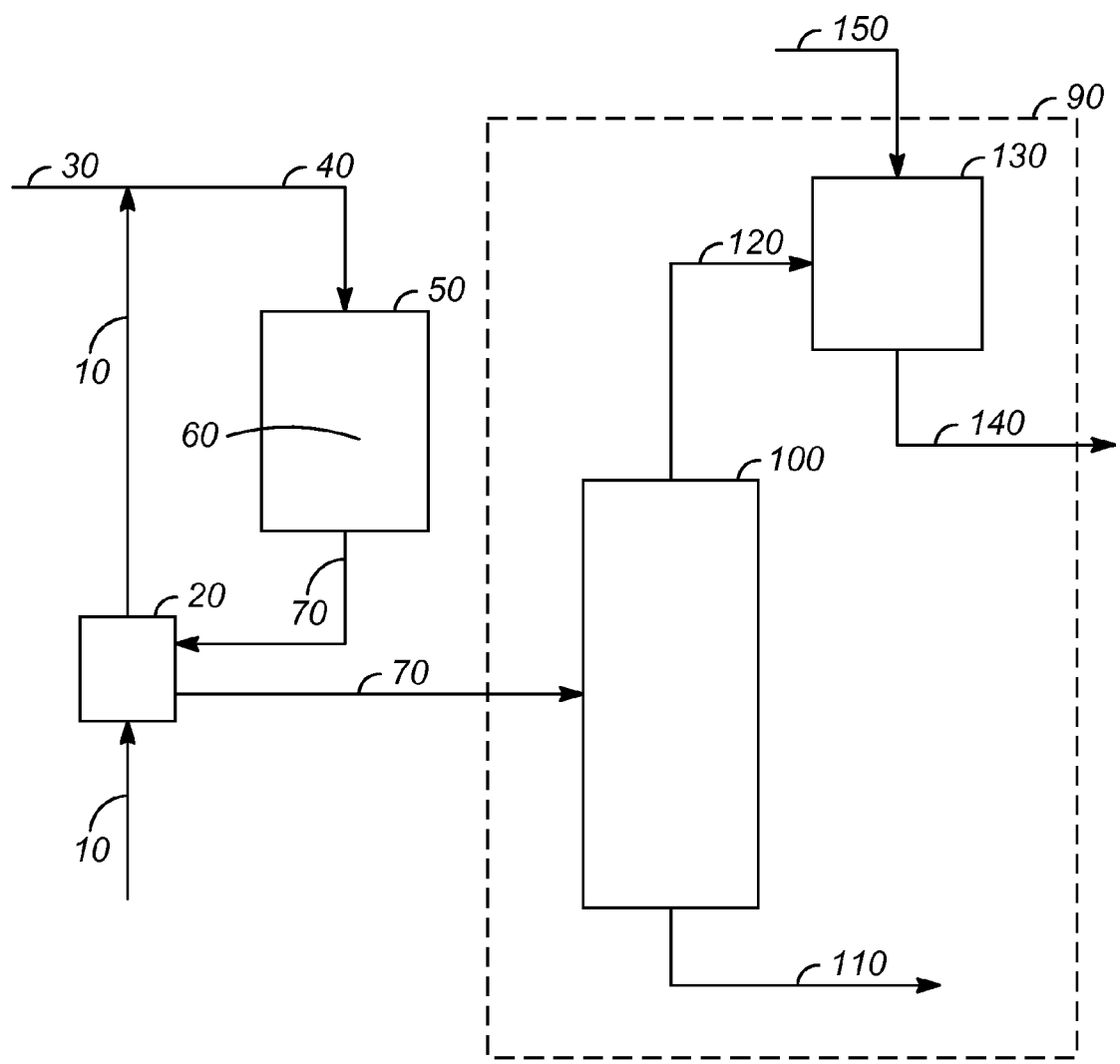

METHODS AND APPARATUSES FOR SELECTIVE HYDROGENATION OF OLEFINS

FIELD

The present subject matter relates generally to methods and apparatuses for selective hydrogenation of olefins contained in a hydrocarbon stream comprising olefins and aromatic compounds. More specifically, the present subject matter relates to methods and apparatuses for selective hydrogenation of olefins contained in a hydrocarbon stream comprising olefins and aromatic compounds without significant hydrogenation of the aromatic compounds.

BACKGROUND

The field of art to which this subject matter pertains is the selective hydrogenation of olefins contained in a hydrocarbon stream comprising olefins and aromatic compounds. Hydrogenation processes have been used by petroleum refiners and petrochemical producers to produce more valuable hydrocarbonaceous products. Hydrocarbonaceous streams containing olefins and aromatic compounds are only useful if the olefins can be selectively hydrogenated without the simultaneous hydrogenation of the aromatic compounds.

The higher reformer severity and lower pressure required for higher aromatics yield also promotes the formation of olefins. The resulting olefins, which are about 1-2 weight percent of the net reformate, contributes to undesirable gum and high endpoint in gasoline product as well as high clay consumption in aromatics recovery operations. Traditionally, clay treating is used when treating aromatics streams to reduce olefin content and meet feed specifications of downstream aromatics processes. However, clay treating is not ideal as it requires hazardous landfill disposal of clay, and results in the loss of valuable aromatics by alkylation with olefins.

Although a wide variety of process flow schemes, operating conditions and catalysts have been used in the selective hydrogenation of olefinic hydrocarbons, there is always a demand for new selective hydrogenation methods which provide lower costs and the required product quality, while minimizing undesirable by-products.

Accordingly, it is desirable to develop methods and apparatuses for selective hydrogenation of olefins that maximizes the production of aromatics. Furthermore, other desirable features and characteristics of the present embodiment will become apparent from the subsequent detailed description and the appended claims, taken in conjunction with the accompanying drawings and this background.

SUMMARY

Methods and apparatuses for selective hydrogenation of olefins are provided. The method for selective hydrogenation of olefins comprises reacting a hydrocarbonaceous feedstock including olefins and aromatic compounds with hydrogen in a reaction zone. The hydrocarbonaceous feedstock may also include paraffins and naphthenes, but is mainly rich in aromatics. The reaction contains a catalyst producing a reaction zone product stream comprising aromatic compounds. The reaction zone product stream is passed to a flash vessel, recovering a first product stream and a second product stream from the flash vessel. The first product stream is passed to a liquid jet eductor, whereas the second product stream comprising aromatic compounds having a reduced concentration of olefins is subsequently recovered.

Hydrocarbonaceous streams, which contain aromatic compounds and olefins, are utilized in downstream processing. Here, the presence of olefins is detrimental to the catalysts used in subsequent processing or is undesirable in product streams. Therefore, it is preferred and desirable that when such hydrocarbon streams are used, the olefins are selectively saturated while preventing or at least minimizing the saturation of the aromatic compounds. Suitable hydrocarbonaceous streams may be derived from any source and a common source for such a hydrocarbonaceous stream is the liquid effluent from a catalytic reformer processing a naphtha feedstock. In the case of a catalytic reformer effluent stream, the aromatic compounds are valuable while the co-produced olefins are considered to be contaminants. However, the co-produced olefins may be removed while preserving the aromatic compounds. The present selective hydrogenation process is employed to reduce the concentration of olefins in a hydrocarbonaceous feedstock containing aromatic compounds and olefins.

Accordingly, a process is presented for the selective hydrogenation of olefins comprising contacting a feed containing aromatic compounds and olefins in a reaction zone at selective hydrogenation conditions with a catalyst comprising elemental nickel to produce a product substantially free of olefinic compounds. The selective hydrogenation conditions include a temperature from about 40° C. (104° F.) to about 130° C. (266° F.), a pressure from about 35 kPa (5 psig) to about 3500 kPa (508 psig) and a stoichiometric ratio of hydrogen to olefins from about 2.5:1 to about 0.8:1. The optimum set of conditions will be selected from these conditions and depend on the composition of the feed stream. In any event, the product from the selective hydrogenation reaction zone will be substantially free of olefins. The term "substantially free" means less than 1000 wppm weight basis of the olefinic compounds (0.1 weight percent). In addition, it is preferred that less than 0.5 weight percent of the aromatic compounds in the hydrocarbonaceous feedstock are hydrogenated.

An advantage of the process for selective hydrogenation of olefins is that olefins are saturated while minimizing the saturation of the desired aromatics.

Another advantage of the methods process for selective hydrogenation of olefins is that the flow scheme eliminates the need of a downstream stripper and its overhead system that usually comprises of a condenser, receiver, and reflux pump.

Yet a further advantage of the methods process for selective hydrogenation of olefins is that it reduces the cost of the selective hydrogenation unit.

Another advantage of the methods process for selective hydrogenation of olefins is that it increases aromatic product yields.

A further advantage of the methods process for selective hydrogenation of olefins is that the dissolved hydrogen is released and recovered in the net gas section of the catalytic reforming unit.

Another advantage of the methods process for selective hydrogenation of olefins is that the number of trays required in the flash vessel reduced.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

Definitions

As used herein, the term "stream", "feed", "product", "part" or "portion" can be used interchangeably and include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated $C_1$, $C_2$, $C_3$. Cn where "n" represents the number of carbon atoms in the one or more hydrocarbon molecules or the abbreviation may be used as an adjective for, e.g., non-aromatics or compounds. Similarly, aromatic compounds may be abbreviated $A_6$, $A_7$, $A_8$. $A_n$ where "n" represents the number of carbon atoms in the one or more aromatic molecules. Furthermore, a superscript "+" or "−" may be used with an abbreviated one or more hydrocarbons notation, e.g., $C_{3=}$ or $C_{3-}$, which is inclusive of the abbreviated one or more hydrocarbons. As an example, the abbreviation "$C_{3+}$" means one or more hydrocarbon molecules of three or more carbon atoms.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

BRIEF DESCRIPTION OF THE DRAWINGS

The drawing FIGURES depict one or more implementations in accord with the present concepts, by way of example only, not by way of limitations. In the FIGURES, like reference numerals refer to the same or similar elements.

The FIGURE is a flow diagram illustrating an example of a process for selective hydrogenation of olefins.

DETAILED DESCRIPTION

The various embodiments described herein relate to methods and apparatuses for selective hydrogenation of olefins. It has been discovered that improved selective hydrogenation of olefins may be achieved by reacting a hydrocarbonaceous feedstock containing olefins and aromatic compounds with a catalyst comprising elemental nickel at mild operating conditions and a limited stoichiometric ratio of hydrogen to olefins.

Although the present subject matter is particularly useful for the selective hydrogenation of olefins contained in naphtha boiling range hydrocarbonaceous streams, any suitable hydrocarbonaceous feedstock may be used in the present example. A preferred feedstock is a naphtha boiling in the range from 50° C. (122° F.) to about 220° C. (428° F.) and containing olefins in an amount from about 0.05 to about 10 weight percent.

Accordingly, a process is presented for the selective hydrogenation of olefins comprising contacting a feed containing aromatic compounds and olefins in a reaction zone at selective hydrogenation conditions with a catalyst comprising elemental nickel to produce a product substantially free of olefinic compounds. The selective hydrogenation conditions include a temperature from about 40° C. (104° F.) to about 130° C. (266° F.), a pressure from about 35 kPa (5 psig) to about 3500 kPa (508 psig) and a stoichiometric ratio of hydrogen to olefins from about 2.5:1 to about 0.8:1. The optimum set of conditions will be selected from these conditions and depend on the composition of the feed steam. In any event, the product from the selective hydrogenation reaction zone will be substantially free of olefins. The term "substantially free" means less than 1000 wppm weight basis of the olefinic compounds (0.1 weight percent). In addition, it is preferred that less than 0.5 weight percent of the aromatic compounds in the hydrocarbonaceous feedstock are hydrogenated.

As shown in the FIGURE, the hydrocarbonaceous feedstock 10 containing olefins and aromatic compounds is introduced along with a hydrogen stream 30 to create a stream 40 that enters a reaction zone 50. The hydrocarbonaceous feedstock 10 may also include paraffins and naphthenes, but is mainly rich in aromatics. In the example illustrated in the FIGURE, the feed 10 and the hydrogen stream 30 are admixed to create stream 40 before entering the reaction zone 50. However, it is also contemplated that the feed 10 and the hydrogen 30 may enter the reaction zone 50 at separate distinct inlets.

The reaction zone 50 contains a selective hydrogenation catalyst 60 comprising elemental nickel and operated at selective hydrogenation conditions including a temperature from about 40° C. (104° F.) to about 130° C. (266° F.), a pressure from about 35 kPa (5 psig) to about 3500 kPa (508 psig), and a stoichiometric ratio of hydrogen to olefins from about 2.5:1 to about 0.8:1. The reaction zone 50 may have more than one reactor. For example, it is contemplated that the reaction zone 50 may have two or more reactors. The reactors may be fixed bed reactors. If there are two reactors, the reactors may be operated in a lead/lag configuration. Therefore, the first reactor is inline always to remove olefins from hydrocarbon stream. Then the second reactor may be taken offline for either catalyst regeneration or catalyst unloading. The multiple reactors may contain the same selective hydrogenation catalyst.

Suitable selective hydrogenation catalysts in the example in the FIGURE may contain elemental nickel preferably supported on a high surface area support material, preferably alumina, such as the catalyst used in U.S. Pat. No. 6,977,317. However, it is contemplated that other catalysts may be used.

According to the present example illustrated in the FIGURE, the selective hydrogenation catalyst 60 is preferably employed in a fixed bed reactor containing a cylindrical bed of catalyst through which the reactants move in a vertical direction. The catalyst may be present within the reactor as pellets, spheres, extrudates, or irregular shaped granules, for example. To employ the catalyst, the reactants would be preferably brought up to the desired inlet temperature of the reaction zone 50, admixed with hydrogen 30 and then passed into and through the reaction zone 50.

Alternatively, the reactants may be admixed with the desired amount of hydrogen and then heated to the desired inlet temperature. In either case, the effluent 70 of the reaction zone 50 may be passed into a product recovery zone 90 for the removal of residual hydrogen or may be passed directly into downstream product utilization zones if the presence of residual hydrogen, if any, is acceptable. As shown in the FIGURE, before the reaction zone effluent stream 70 is sent to the product recovery zone 90, the reactor effluent stream 70 may be passed through a heat exchanger 20 which reduces the reaction zone effluent stream 70 temperature and pressure, thus passing the reaction zone effluent stream 70 to the product recovery zone 90 in a more suitable condition. However, it is also contemplated that the reactor zone effluent stream 70 may pass directly to the product recovery zone 90. Once the reactor zone effluent stream 70 enters the product recovery zone 90, the hydrogen may be removed by flashing the effluent stream 70 to a lower pressure or by passing the effluent stream into a flash vessel 90 such as a stripping or a single stage flash column.

In the example shown in the FIGURE, the flash vessel 100 may comprise four or more vapor-liquid contacting trays or equivalent packing. In the example shown in the FIGURE, the reaction zone effluent 70 may enter the top tray of the flash vessel 100. However, it is contemplated that the reaction zone effluent 70 may enter the flash vessel 100 at other locations. The flash vessel 100 produces an aromatic product stream 110 having a reduced concentration of olefins. The flash vessel 100 also produces a light product stream 120 that is mainly rich in hydrogen that enters a liquid jet eductor 130 along with a liquid stream 150. The liquid jet eductor 130 produces an eductor product stream 140. The eductor product stream 140 may then be directed back to a low pressure separator located in the reactor section of a continuous catalytic reforming unit. A liquid stream 150 is used as a motive fluid in the jet eductor 130. As mentioned earlier, the bottom product stream 110 from the flash vessel 100 may be sent to an aromatics complex.

The operating pressure of the flash vessel 100 is kept at battery limit pressure required for downstream units in the aromatic complex and it is in a range of 200 to 1100 kPa(g). The operating temperature is in a range of 70-180 deg C. (158-356° F.) so that any release of unreacted hydrogen in flash vessel 100 is removed in the overhead light product stream 120 and there is no further flashing in the downstream units.

As shown in Table 1, a simulation study was carried out with varying hydrogen to olefins ratio and varying operating temperatures. This study indicated that at lower pressure (~1030 kPa(g)) and moderate temperature (70-180 Deg C.). The amount of hydrogen release from liquid phase hydrocarbons is less due to higher hydrogen solubility at these conditions.

TABLE 1

Hydrogen Flash Study at Various Hydrogen to Olefin Ratios and Operating Temperatures

| H2:Olefins molar ratio in reactor effluent stream | Stripper Pressure (kpa (g)) | Stripper Temperature (deg C.) | H2 in reactor effluent stream (lbmol/hr) | H2 in overhead vapor stream (lbmol/hr) | % H2 recovery in overhead vapor stream |
|---|---|---|---|---|---|
| 0.5 | 1030 | 110 | 5.30 | 0.00 | 0.00 |
| 0.5 | 1030 | 90 | 5.30 | 0.00 | 0.00 |
| 0.5 | 1030 | 80 | 5.30 | 0.00 | 0.00 |
| 0.5 | 1030 | 75 | 5.30 | 0.09 | 1.74 |
| 0.5 | 1030 | 70 | 5.30 | 0.22 | 4.15 |
| 1.0 | 1030 | 110 | 10.60 | 5.40 | 50.94 |
| 1.0 | 1030 | 90 | 10.60 | 5.50 | 51.89 |
| 1.0 | 1030 | 80 | 10.60 | 5.60 | 52.83 |
| 1.0 | 1030 | 75 | 10.60 | 5.70 | 53.77 |
| 1.0 | 1030 | 70 | 10.60 | 5.80 | 54.72 |
| 1.5 | 1030 | 110 | 15.90 | 11.60 | 72.96 |
| 1.5 | 1030 | 90 | 15.90 | 11.29 | 71.01 |
| 1.5 | 1030 | 80 | 15.90 | 11.31 | 71.13 |
| 1.5 | 1030 | 75 | 15.90 | 11.30 | 71.07 |
| 1.5 | 1030 | 70 | 15.90 | 11.37 | 71.51 |

As shown in Table 1, hydrogen starts releasing from liquid phase below 75° C. for molar ratio of 0.5 in the reactor effluent. The feed rate is 1060 lbmol/hr with 1% total olefins in the feed. As long as the operating temperature of flash vessel remains in the range of 70-180° C. (158-356° F.), there is no release of hydrogen. If the flash vessel is operated at higher hydrogen to olefins ratio or there is less conversion in the upstream reaction zone, the excess hydrogen release in the flash vessel will be captured by the liquid jet eductor. The outlet stream from jet eductor is then sent to low pressure separator in the continuous catalytic reforming unit and the excess hydrogen from the separator will get recovered with the net gas in the recontact section.

It is contemplated that the process for selective hydrogenation of olefins may be used to reduce the olefins from a variety of feeds. In one example, the feed may come from a catalytic reforming unit debutanizer feed. Here, the process for selective hydrogenation of olefins would treat the entire reformate stream including the $C_{5-}$, the aromatics extraction unit feed ($C_5$-$C_7$), and $C_{8+}$. In this example, the raffinate requires that olefins be removed, usually reduced to less than 1.0 wt %, and there is need to remove olefins from the $C_{8+}$ either for the recovery of para-xylene or mixed xylenes production. In this example, a stripper or flash drum is not required because the reactor effluent goes to the catalytic reforming unit debutanizer (stabilizer) which does the stripping.

In yet another example, the feed may come from a catalytic reforming unit debutanizer bottoms or reformate splitter. Here, the selective hydrogenation of olefins treats the aromatics extraction unit feed and $C_{8+}$, where the feed comprises $C_5$ through $C_{8+}$. However, in this position a stripper or flash drum is required because there is no stripping column downstream. The advantage of this position is that the hydrogen consumption is reduced since the $C_{4-}$ olefins have been removed from the feed.

In yet another example, the feed may come from a reformate splitter overhead or aromatics extraction unit feed. Here, the selective hydrogenation of olefins treats only the aromatics extraction unit feed. In this example, the process is used if the aromatics extraction unit raffinate has an olefins spec but there is no need to use the process on the $C_{8+}$ stream. The process may also treat the aromatics extraction unit raffinate stream directly but this is usually not chosen because the olefins content of the raffinate is essentially the same as the aromatics extraction unit feed.

In yet another example, the feed may come from a reformate splitter bottoms. Here, the selective hydrogenation of olefins treats only the $C_{8+}$. The process is used if the aromatics extraction unit raffinate does not require the olefins to be removed but there is need to remove olefins from the $C_{8+}$ either for recovery of para-xylene or mixed xylenes production. In this position a stripper or flash drum may be required if there is no stripping column downstream.

In yet another example, the feed may come from a xylene column overhead. Here, the selective hydrogenation of olefins treats only the $C_8$, for example, either the para-xylene or mixed xylenes product. The advantage of this position is that the hydrogen consumption is low because the $C_{9+}$ olefins have been removed from the feed. In this position a stripper or flash drum may be required if there is no stripping column downstream.

It should be noted that various changes and modifications to the presently preferred embodiments described herein will be apparent to those skilled in the art. Such changes and modifications may be made without departing from the spirit and scope of the present subject matter and without diminishing its attendant advantages.

The invention claimed is:

1. A method for selective hydrogenation of olefins comprising:
    reacting a hydrocarbonaceous feedstock comprising olefins and aromatic compounds with hydrogen in a reaction zone containing a catalyst producing a reaction zone product stream comprising aromatic compounds;
    passing the reaction zone product stream to a flash vessel;
    recovering a first product stream and a second product stream from the flash vessel operating at a temperature from about 70-180° C. (158-356° F.); and
    passing the first product stream to a liquid jet eductor;
    wherein the second product stream comprises aromatic compounds having a reduced concentration of olefins.

2. The method of claim 1 wherein the hydrocarbonaceous feedstock is a naphtha boiling range stream.

3. The method of claim 1 wherein the feedstock contains olefins in an amount from about 0.05 weight percent to about 10 weight percent.

4. The method of claim 1 wherein the catalyst is a selective hydrogenation catalyst comprising a layered structure having an inner core, an outer layer, and at least one metal.

5. The method of claim 1 wherein the reaction zone contains one or more reactors.

6. The method of claim 1 wherein the reaction zone product stream passes through a heat exchanger which reduces temperature and pressure of the reaction zone product stream before entering the flash vessel.

7. The method of claim 1, wherein the flash vessel comprises four or more vapor-liquid contacting trays or equivalent packing.

8. The method of claim 1, wherein the reaction zone operates at a temperature from about 40° C. (104° F.) to about 130° C. (266° F.).

9. The method of claim 1, wherein the reaction zone operates at a pressure from about 35 kPa (5 psig) to about 3500 kPa (508 psig).

10. The method of claim 1, wherein the reaction zone operates at a stoichiometric ratio of hydrogen to olefins from about 2.5:1 to about 0.8:1.

11. The method of claim 1, wherein the flash vessel operates at a pressure from about 200-1100 kPa(g) (29-160 psig).

12. The method of claim 1, further comprising an outlet stream from the liquid jet eductor wherein the outlet stream is sent to a low pressure separator in a continuous catalytic reforming unit in order to recover hydrogen and light hydrocarbons.

13. The method of claim 1, wherein the flash vessel operates at a temperature from about 80-110° C.

14. A method for selective hydrogenation of olefins comprising:
    reacting a naphtha boiling range stream comprising olefins and aromatics wherein the olefins comprise about 0.05 weight percent to about 10 weight percent with hydrogen in a selective hydrogenation zone having a reactor where the reactor contains a catalyst producing a selective hydrogenation zone product stream comprising aromatic compounds;
    passing the selective hydrogenation zone product stream to a flash vessel wherein the flash vessel comprises four or more vapor-liquid contacting trays or equivalent packing and the flash vessel operates at a temperature from about 70° C. (158° F.) to about 180° C. (356° F.), a pressure from about 200 kPa (29 psig) to about 1100 kPa (160 psig);
    recovering a first product stream and a second product stream from the flash vessel;
    passing the first product stream to a liquid jet eductor; and
    recovering the second product stream comprising aromatic compounds having a reduced concentration of olefins.

15. The method of claim 14, wherein the selective hydrogenation zone operates at a stoichiometric ratio of hydrogen to olefins from about 2.5:1 to about 0.8:1.

16. The method of claim 14 wherein the catalyst is a selective hydrogenation catalyst comprising a layered structure having an inner core, an outer layer, and a metal.

17. The method of claim 14 wherein the selective hydrogenation zone contains more than one reactor.

18. The method of claim 14 wherein the selective hydrogenation zone product stream passes through a heat exchanger which reduces temperature and pressure of the selective hydrogenation zone product stream before entering the flash vessel.

19. The method of claim 14, further comprising an outlet stream from the liquid jet eductor wherein the outlet stream is sent to a low pressure separator in a continuous catalytic reforming unit in order to recover hydrogen and light hydrocarbons.

* * * * *